United States Patent [19]

Schulze et al.

[11] 4,209,446
[45] Jun. 24, 1980

[54] PROCESS FOR THE PREPARATION OF PIPERONYLIDENECROTONIC ACID AMIDES

[75] Inventors: Andreas Schulze; Hermann Oediger, both of Cologne, Fed. Rep. of Germany

[73] Assignee: Haarman & Reimer GmbH, Holzminden, Fed. Rep. of Germany

[21] Appl. No.: 969,114

[22] Filed: Dec. 13, 1978

[30] Foreign Application Priority Data

Dec. 22, 1977 [DE] Fed. Rep. of Germany ....... 2757506

[51] Int. Cl.$^2$ ............................................. C07D 317/44
[52] U.S. Cl. .......................... 260/340.5 R; 260/239 B; 260/326.4; 544/109; 546/245
[58] Field of Search ..................... 260/340.5 R, 559 R

[56] References Cited

U.S. PATENT DOCUMENTS

| 2,951,853 | 9/1960 | Matsui et al. ..................... 260/347.5 |
| 4,021,574 | 5/1977 | Bollag et al. ..................... 260/559 R |

Primary Examiner—Ethel G. Love

Attorney, Agent, or Firm—Sprung, Felfe, Horn, Lynch & Kramer

[57] ABSTRACT

Process for the preparation of piperonylidenecrotonic acid amides of the formula

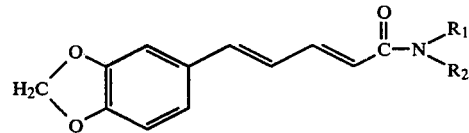

in which $R_1$ and $R_2$ have the meaning given in the disclosure wherein piperonal is reacted with crotonic acid amides of the formula

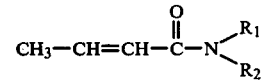

in the presence of alkali metal hydroxides and dipolar aprotic diluents which are inert under the reaction conditions.

3 Claims, No Drawings

PROCESS FOR THE PREPARATION OF PIPERONYLIDENECROTONIC ACID AMIDES

The present invention relates to a new process for the preparation of piperonylidenecrotonic acid amides.

Piperonylidenecrotonic acid amides have diverse industrial uses. Thus piperonylidenecrotonic acid piperidide (trivial name: piperine) is an important aromatic essence. It is the hot ingredient of black pepper (Chromatographia Volume 8 (1975), pages 342-344). Further suitable aromatic essences for rounding off the flavour of pepper formulations are piperonylidenecrotonic acid pyrrolidide, also called piperyline (Chem. Ber. Volume 103 (1970), pages 3,752-3,770) and piperonylidenecrotonic acid isobutylamide, also called piperlonguminine (Tetrahedron Volume 23 (1967), pages 1,769-1,781). Piperine is also used as an additive to germicidal formulations (U.S. Pat. No. 2,085,064). Piperonylidenecrotonic acid amides are also suitable as insecticides or synergistic agents for insecticides (U.S. Pat. No. 2,487,179; Contrib. Boyce Thompson Inst. Volume 13 (1945) pages 433-442; Russian Patent No. 222,056; and DT-OS (German Published Specification) No. 2,413,756). Furthermore, piperine is also suitable as an analeptic agent in cases of morphine or barbiturate poisoning (J. Res. Indian Med. Volume 8 (1973), pages 1-9 and Volume 9 (1974) pages 17-22 ).

Various processes have therefore already been proposed for the preparation of piperonylidenecrotonic acid amides, in particular of piperine. Thus, according to one preparation process, piperonal is first converted into piperonylideneacetaldehyde in a three-stage process, this compound is subjected to a condensation reaction with a malonic acid half-ester to give the piperonylidenecrotonic acid ester and this ester is converted into the corresponding piperidide by means of piperidine via three further stages (Chem. Ber. Volume 108 (1975), pages 95-108).

However, because of its many process steps and the unsatisfactory yields—the total yield is only 41%—this process is uneconomical and therefore cannot be used for preparing piperine on an industrial scale.

Piperine has also been prepared by condensation of piperonylideneacetaldehyde with piperidinocarbonylmethyltriphenylphosphonium iodide (Pharm. Chem. J. Volume 5 (1971), pages 462 to 464). However, this preparation has the disadvantage that the compounds to be employed as the reactants must in turn first be prepared by multi-stage processes, and that large amounts of triphenylphosphine oxide are formed during the condensation and can be separated off from the piperine only with difficulty. This process is therefore also unsuitable for synthesising piperine on an industrial scale.

It has now been found that known and new piperonylidenecrotonic acid amides of the formula

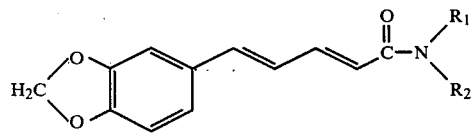

in which $R_1$ and $R_2$ independently of one another represent hydrogen or an optionally substituted aliphatic, araliphatic or aromatic hydrocarbon radical, or, together with the nitrogen atom, form a heterocyclic ring, with the proviso that $R_1$ and $R_2$ do not simultaneously denote hydrogen, can be prepared in excellent yields in a simple manner when piperonal is reacted with crotonic acid amides of the formula

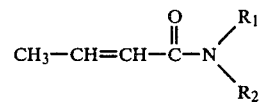

in which $R_1$ and $R_2$ have the meaning indicated above, in the presence of alkali metal hydroxides and dipolar aprotic diluents which are inert under the reaction conditions.

Compared with the processes known from the state of the art, the process according to the invention is distinguished by a considerably simplified procedure (few reaction stages and the use of condensation agents which can be handled industrially without special safety measures) and by substantially improved yields. Piperonylidenecrotonic acid amides can be prepared on an industrial scale without difficulty by the process according to the invention. The compounds are obtained in high purity.

It was in fact already known to subject aldehydes to condensation reactions with 3-methylbutenecarboxylic acid esters, 3-methylbutenecarboxylic acid amides or crotonic aid esters (U.S. Pat. No. 2,951,853; and Chem. Ber. Volume 106 (1973), pages 2,643-2,647). However, the condensation reactions were carried out using at least equimolar amounts, relative to the amount of alkenoic acid ester, of powerful condensation agents such as alkali metals, alkali metal amides, alkali metal hydrides or organometallic compounds, such as phenylsodium or triphenylmethylpotassium, and with complete exclusion of water.

It was therefore surprising that the reaction according to the invention already proceeds in high yields, even without exclusion of water, with catalytic amounts of condensation agents which are known to have a weaker action, such as sodium hydroxide or potassium hydroxide. In view of the fact that the reactivity of piperonal is comparable to that of 4-methoxybenzaldehyde, and since it was known that deactivated aldehydes such as 4-methoxybenzaldehyde react with crotonic acid ethyl ester to give the desired condensation product in only 12% yield, even in the presence of powerful condensation agents such as sodium amide (Chem. Ber. Volume 106 (1973), pages 2,643-2,647), it was to be expected that no reaction at all would take place under the reaction conditions according to the invention.

Furthermore, it was known that piperonal can undergo condensation with ethylidenemalonic acid esters using potassium hydroxide in ethanol (J. Am. Soc. Volume 74 (1952), pages 5,527-5,529). However, if in this reaction the ethylidenemalonic acid ester, which is known to be very reactive, is replaced by crotonic acid amides, which are considerably slower to react, the yields of condensation product decrease to such an extent (down to about 10% of theory) that this reaction is of no interest for the preparation of piperonylidenecrotonic acid amides.

It is an essential characteristic of the surprisingly favourable course of the condensation reaction, according to the invention, of piperonal with crotonic acid amides that this condensation is not carried out in nonpolar or polar protic organic diluents, as in the above-mentioned condensation reactions, but in dipolar aprotic organic diluents.

Examples which may be mentioned of dipolar aprotic organic diluents which are inert under the reaction conditions are: acid amides, for example dialkylformamides or dialkylacetamides, such as dimethylformamide or dimethylacetamide, or 1-methyl-2-pyrrolidinone; tetraalkylureas, such as tetramethylurea; sulphoxides, for example dialkylsulphoxides, such as dimethylsulphoxide, and tetrahydrothiophene 1-oxide; sulphones, such as tetrahydrothiophene 1,1-dioxide; hexaalkylphosphoric acid triamides, such as hexamethylphosphoric acid triamide; or 1-methyl-1-oxophospholine. Dimethylsulphoxide has proved particularly suitable.

The amounts in which the dipolar aprotic organic diluents are employed can vary within wide limits; in general, it has proved suitable to employ 50–500, preferably 100–350, ml of diluent per mol of piperonal. It is possible to increase the amount of diluent above the maximum amount mentioned of 500 ml, but this is of no advantage.

Of the alkali metal hydroxides, such as lithium hydroxide, sodium hydroxide and potassium hydroxide, which can be used as condensation agents in the process according to the invention, sodium hydroxide and potassium hydroxide, above all, are employed. Potassium hydroxide has proved particularly suitable.

The alkali metal hydroxides can be employed either as anhydrous compounds or in the form of aqueous solutions, for example 40 to 50% strength aqueous solutions.

In general, the alkali metal hydroxides are used in amounts of 0.05–0.5 mol, preferably 0.1–0.2 mol, per mol of piperonal.

In general, the condensation according to the invention is carried out at temperatures between $-10°$ C. and $+70°$ C., preferably between $+10°$ C. and $+30°$ C. If very small amounts of diluent and alkali metal hydroxide are used, reaction temperatures of 65°–70° C. can be advantageous.

The reaction can be carried out under normal pressure or increased pressure. In general, it is carried out under normal pressure. It is preferably carried out in an inert gas atmosphere, for example under nitrogen or argon.

The two reactants are appropriately employed in the process according to the invention in approximately equimolar amounts; it has proved suitable to use 1 to 1.2 mols of crotonic acid amide, preferably 1 to 1.1 mols of crotonic acid amide, per mol of piperonal.

The piperonylidenecrotonic acid amides in general separate out as solid precipitates in the course of the reaction, in the process according to the invention. These precipitates can be purified by recrystallisation. The diluent obtained after filtering off the piperonylidenecrotonic acid amide precipitate can be re-used without purification.

The course of the process according to the invention may be illustrated by the equation which follows:

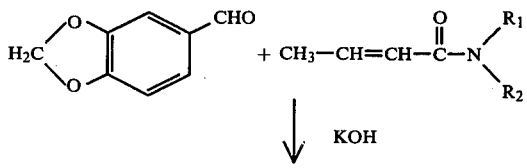

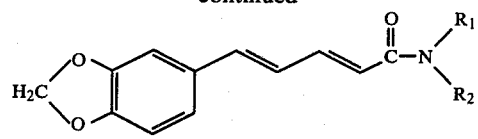

For $R_1$ and $R_2$, examples of optionally substituted aliphatic hydrocarbon radicals which may be mentioned are, above all, $C_1$–$C_6$-alkyl radicals, $C_1$–$C_6$-alkenyl radicals and 5-membered and 6-membered cycloalkyl radicals, for example the methyl, ethyl, n-propyl, i-propyl, n-butyl, sec.-butyl, i-pentyl, n-hexyl, i-hexyl, allyl, cyclopentyl and cyclohexyl radical, and furthermore cyclopentyl and cyclohexyl radicals substituted by $C_1$–$C_4$-alkyl groups, such as the 4-methyl- and 2,4-dimethyl-cyclohexyl radical, possible substituents of the alkyl radicals being, above all, halogen atoms, such as the chlorine atom, and the hydroxyl group and examples of substituted alkyl radicals being the 2-chloroethyl and 2-hydroxyethyl radical; examples which may be mentioned of optionally substituted araliphatic and aromatic hydrocarbon radicals are, above all, the benzyl and phenyl radical and benzyl and phenyl radicals which are substituted by halogen atoms, for example chlorine or bromine atoms, or by $C_1$–$C_4$-alkyl groups and $C_1$–$C_4$-alkoxy groups, such as the 4-methyl- and 3-chloro-benzyl radical and the 3-chloro, 2,4-dichloro-, 2-bromo-4-methyl-, 4-ethyl- and 4-methoxy-phenyl radical; and examples which may be mentioned of heterocyclic rings which $R_1$ and $R_2$ can form, together with the amide nitrogen, are, above all, 5-membered to 7-membered heterocyclic rings optionally containing further hetero-atoms, such as oxygen, sulphur or nitrogen, such as the piperidine, pyrrolidine, morpholine and hexamethyleneimine ring, it also being possible for these heterocyclic rings to be substituted, for example by $C_1$–$C_4$-alkyl groups, examples being 2-, 3- and 4-methylpiperidine, 2,3-, 2,4- and 2,6-dimethylpiperidine, 2-ethyl-piperidine and 2,4,6-trimethylpiperidine.

The crotonic acid amides to be used, according to the invention, as starting compounds are known or can be prepared by processes which are in themselves known, for example from crotonoyl chloride and the corresponding amines (Helv. Chim. Acta Volume 38 (1955), pages 1,085–1,095) or from the corresponding ammonium salts of crotonic acid, either by splitting off water at elevated temperature, optionally in the presence of acid catalysts, or by reaction with inorganic acid halides, for example thionyl chloride (Houben-Weyl, Methoden der organischen Chemie (Methods of Organic Chemistry), Volume XI/2, pages 3–9, Thieme Verlag Stuttgart 1958).

Examples which may be mentioned of representatives of the crotonic acid amides to be reacted according to the invention are: crotonic acid piperidide, crotonic acid pyrrolidide, crotonic acid morpholide, crotonic acid hexamethyleneimide, crotonic acid 2-methylpiperidide, crotonic acid 3-methylpiperidide, crotonic acid 4-methylpiperidide, crotonic acid 2-pentylpiperidide, crotonic acid 4-pentylpiperidide, crotonic acid 2,4,6-trimethylpiperidide, crotonic acid 2,6-dimethylpiperidide, crotonic acid 2,4-dimethylpiperidide, crotonic acid 2-ethylpiperidide, crotonic acid 2,3-dimethylpiperidide, crotonic acid methylamide, crotonic acid ethylamide, crotonic acid propylamide, crotonic acid allylamide, crotonic acid butylamide, crotonic acid isobutylamide, crotonic acid isopentylamide, crotonic acid cyclohexylamide, crotonic acid 3-ethyl-heptylamide, crotonic acid benzylamide, crotonic acid 3,4-methylenedioxy-anilide, crotonic acid anilide, crotonic acid 2-bromo-4-methyl-anilide, crotonic acid dimethylamide, crotonic acid diethylamide, crotonic acid dipropylamide, crotonic acid diisopropylamide, crotonic acid diallylamide, crotonic acid dibutylamide, crotonic acid diisobutylamide, crotonic acid dicyclohexylamide, crotonic acid di-β-chloroethyl-amide and crotonic acid di-β-hydroxyethyl-amide.

Examples which may be mentioned of representatives of the piperonylidenecrotonic acid amides which can be prepared by the process according to the invention are: piperonylidenecrotonic acid piperidide, piperonylidenecrotonic acid pyrrolidide, piperonylidenecrotonic acid morpholide, piperonylidenecrotonic acid hexamethyleneimide, piperonylidenecrotonic acid 2-methylpiperidide, piperonylidenecrotonic acid 3-methylpiperidide, piperonylidenecrotonic acid 4-methylpiperidide, piperonylidenecrotonic acid 2-pentylpiperidide, piperonylidenecrotonic acid 4-pentylpiperidide, piperonylidenecrotonic acid 2,4,6-trimethylpiperidide, piperonylidenecrotonic acid 2,6-dimethylpiperidide, piperonylidenecrotonic acid 2,4-dimethylpiperidide, piperonylidenecrotonic acid 2-ethylpiperidide, piperonylidenecrotonic acid 2,3-dimethylpiperidide, piperonylidenecrotonic acid methylamide, piperonylidenecrotonic acid ethylamide, piperonylidenecrotonic acid propylamide, piperonylidenecrotonic acid allylamide, piperonylidenecrotonic acid butylamide, piperonylidenecrotonic acid isobutylamide, piperonylidenecrotonic acid isopentylamide, piperonylidenecrotonic acid cyclohexylamide, piperonylidenecrotonic acid 3-ethyl-heptylamide, piperonylidenecrotonic acid benzylamide, piperonylidenecrotonic acid 3,4-methylenedioxy-anilide, piperonylidenecrotonic acid anilide, piperonylidenecrotonic acid 2-bromo-4-methyl-anilide, piperonylidenecrotonic acid dimethylamide, piperonylidenecrotonic acid diethylamide, piperonylidenecrotonic acid dipropylamide, piperonylidenecrotonic acid diisopropylamide, piperonylidenecrotonic acid diallylamide, piperonylidenecrotonic acid dibutylamide, piperonylidenecrotonic acid diisobutylamide, piperonylidenecrotonic acid dicyclohexylamide, piperonylidenecrotonic acid di-β-chloroethyl-amide and piperonylidenecrotonic acid di-β-hydroxyethyl-amide.

The parts indicated in the examples which follow are parts by weight, unless it has been indicated otherwise.

EXAMPLE 1

2.2 parts (0.04 mol) of powdered potassium hydroxide are added to a solution of 30 parts (0.2 mol) of piperonal and 32 parts (0.209 mol) of crotonic acid piperidide in 50 parts by volume of dimethylsulphoxide at 20° to 25° C. under nitrogen. The reaction mixture is stirred at 25° to 30° C. for 4 hours and then at 25° C. for 10 hours. The precipitate is filtered off, washed with water and dried. Yield: 45.6 parts of crude piperonylidenecrotonic acid piperidide.

After recrystallisation from ethyl acetate, the yield of pure piperonylidenecrotonic acid piperidide is 42 parts (=73% of theory). Melting point 129°–130° C.

Piperonylidenecrotonic acid piperidide was obtained in comparable yield and purity when 50 parts by volume of tetrahydrothiophene 1,1-dioxide, N-methylpyrrolidinone or dimethylformamide were used as the solvent instead of the 50 parts by volume of dimethylsulphoxide.

EXAMPLES 2 to 7

1 mol of piperonal is reacted with 1.05 mols of a crotonic acid amide, indicated in the table below, in the presence of 0.2 mol of potassium hydroxide under the conditions indicated in Example 1. The piperonylidenecrotonic acid amides listed in the table are obtained in the yields likewise indicated in the table.

Table

Formulae of the crotonic acid amides (a) employed and the piperonylidenecrotonic acid amides (b) obtained therefrom (a) $CH_3-CH=CH-C(=O)N(R_1)(R_2)$ (b) piperonylidene-CH=CH-CH=CH-C(=O)N(R_1)(R_2)

| Example No. | $N(R_1)(R_2)$ | Yield in % of theory | Melting point in °C. |
|---|---|---|---|
| 2 | piperidino | 68 | 142–143 |
| 3 | morpholino | 70 | 167–168 |
| 4 | HN—CH$_2$—CH(CH$_3$)$_2$ | 71 | 165–166 |
| 5 | N(C$_2$H$_5$)$_2$ | 69 | 94–95 |
| 6 | N(CH$_2$—CH=CH$_2$)$_2$ | 70 | 75–76 |

Table-continued
Formulae of the crotonic acid amides (a) employed and the piperonylidenecrotonic acid amides (b) obtained therefrom

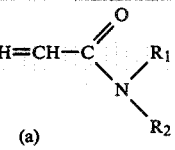
(a)

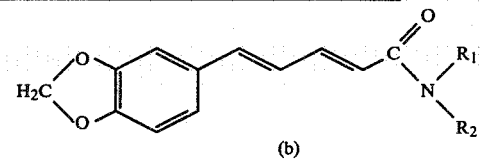
(b)

| Example No. | 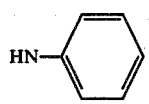 | Yield in % of theory | Melting point in °C. |
|---|---|---|---|
| 7 | 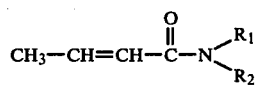 | 72 | 197–198 |

EXAMPLE 8

88 parts of 50% strength potassium hydroxide solution are allowed to run rapidly into a solution of 600 parts of piperonal and 639 parts of crotonic acid piperidide in 1,000 parts by volume of dimethylsulphoxide at 25° C. under nitrogen, whilst stirring vigorously. The temperature of the reaction mixture is kept at 28°–30° C. by cooling, and after the reaction mixture has crystallised out, it is further stirred at room temperature for some time. The crystals are filtered off, washed with water and dried.

911 parts of crude piperonylidenecrotonic acid piperidide are obtained. The crude product is purified by recrystallisation from ethyl acetate. Yield: 870 parts of pure piperonylidenecrotonic acid piperidide (=76% of theory), melting point 129°–130° C.

EXAMPLE 9

0.8 ml of 50% strength aqueous KOH is added to a solution of 15.0 parts (0.1 mol) of piperonal and 17.0 parts (0.11 mol) of crotonic acid piperidide in 10 parts by volume of dimethylsulphoxide at 25° C. The reaction mixture is then stirred at 60°–65° C. for 8 hours. After distilling off the solvent in vacuo, 40 ml of water are added to the reaction mixture. The precipitate is filtered off, washed with water and dried.

After recrystallisation from ethyl acetate, 22 parts (=77% of theory) of pure piperonylidenecrotonic acid piperidide are obtained. Melting point 129°–130° C.

EXAMPLE 10

1.65 parts of 50% strength aqueous sodium hydroxide solution are added to a solution of 15 parts (0.1 mol) of piperonal and 17 parts (0.11 mol) of crotonic acid piperidide in 50 parts by volume of dimethylsulphoxide at 26° C. under nitrogen. The reaction mixture is stirred at 26° to 30° C. for 8 hours and the crystals which are obtained are then filtered off, washed with water and dried. Yield of crude piperonylidenecrotonic acid piperidide: 20 parts.

After recrystallisation from ethyl acetate, the yield of pure piperonylidenecrotonic acid piperidide is 17 parts (=60% of theory). Melting point 129°–130° C.

What is claimed is:

1. A process for the preparation of a piperonylidenecrotonic acid amide of the formula

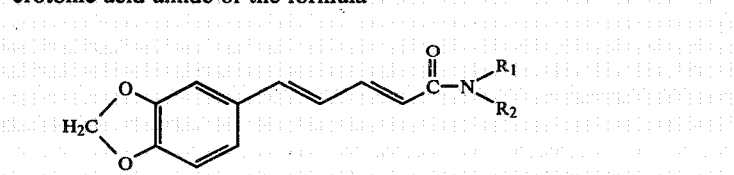

in which $R_1$ and $R_2$ independently of one another represent hydrogen or an optionally substituted aliphatic, araliphatic or aromatic hydrocarbon radical, or, together with the nitrogen atom, form a heterocyclic ring, with the proviso that $R_1$ and $R_2$ do not simultaneously denote hydrogen, comprising reacting piperonal with a crotonic acid amide of the formula $$CH_3-CH=CH-\overset{\overset{O}{\|}}{C}-N\overset{R_1}{\underset{R_2}{<}}$$

in which $R_1$ and $R_2$ have the meaning indicated above, in the presence of 0.05 to 0.5 mol of an alkali metal hydroxide per mol of piperonal and a dipolar aprotic diluent which is inert under the reaction conditions.

2. A process according to claim 1, wherein the inert dipolar aprotic diluent is a dialkylformamide, dialkylacetamide, 1-methyl-2-pyrrolidinone, a tetraalkylurea, a dialkylsulphoxide, a sulphone, a hexaalkyl phosphoric acid triamide or 1-methyl-1-oxo-phospholine.

3. A process according to claim 2, wherein the inert dipolar aprotic diluent is dimethylsulphoxide.

* * * * *